US00PP17865P2

(12) United States Plant Patent
Eskelund Hansen

(10) Patent No.: US PP17,865 P2
(45) Date of Patent: Jul. 17, 2007

(54) ROSE PLANT NAMED 'EVERA 117'

(50) Latin Name: *Rosa hybrida*
Varietal Denomination: Evera 117

(76) Inventor: Rosa Eskelund Hansen, Fiskervaenget 9, 5600 Fåborg (DK)

( * ) Notice: Subject to any disclaimer, the term of this patent is extended or adjusted under 35 U.S.C. 154(b) by 125 days.

(21) Appl. No.: 11/146,199

(22) Filed: Jun. 6, 2005

(51) Int. Cl.
*A01H 5/00* (2006.01)

(52) U.S. Cl. ..... Plt./122
(58) Field of Classification Search ..... Plt./122
See application file for complete search history.

(56) References Cited

U.S. PATENT DOCUMENTS

PP15,853 P2 * 7/2005 Olesen et al. ..... Plt./122

OTHER PUBLICATIONS

UPOV ROM GTITM Computer Database, GTI Jouve Retrieval Software 2006/05 Citation for 'Evera 117'.*

* cited by examiner

*Primary Examiner*—Wendy Haas
(74) *Attorney, Agent, or Firm*—C. A. Whealy

(57) ABSTRACT

A new and distinct cultivar of rose plant named 'Evera 117', characterized by its upright, compact and rounded plant habit; dark green-colored leaves; large bright double red-colored flowers; flowers held upright on strong and erect peduncles; and good postproduction longevity.

2 Drawing Sheets

Botanical designation: *Rosa hybrida.*
Cultivar denomination: 'Evera 117'.

BACKGROUND OF THE INVENTION

The present invention relates to a new and distinct cultivar of the Rose class, botanically known as *Rosa hybrida,* commercially known as a potted Rose and hereinafter referred to by the name 'Evera 117'.

The new Rose plant is a product of a planned breeding program conducted by the Inventor in Denmark. The objective of the breeding program was to develop new potted Rose cultivars with novel and attractive flower colors, disease resistance and excellent postproduction longevity.

The new Rose plant originated from a cross-pollination made by the Inventor on Apr. 1, 2002 of two unnamed proprietary *Rosa hybrida* seedlings, not patented. The cultivar Evera 117 was discovered and selected by the Inventor as a flowering plant within the progeny of the stated cross-pollination in a controlled environment in Denmark. Plants of the new cultivar differ primarily from plants of the parent selections primarily in flower color.

Asexual reproduction of the new Rose plant by cuttings in Denmark since Dec. 1, 2003, has shown that the unique features of this new Rose plant are stable and reproduced true to type in successive generations of asexual reproduction.

SUMMARY OF THE INVENTION

The new Rose plant has not been observed under all possible environmental conditions. The phenotype may vary significantly with variations in environment such as temperature and light level, without, however, any variance in genotype.

The following traits have been repeatedly observed and are determined to be the unique characteristics of 'Evera 117'. These characteristics in combination distinguish the new Rose plant as a new and distinct cultivar:

1. Upright, compact and rounded plant habit.
2. Dark green-colored leaves.
3. Large double bright red-colored flowers.
4. Flowers held upright on strong and erect peduncles.
5. Good postproduction longevity.

Plants of the new Rose plant can be compared to plants of the Rose cultivar Espever, not patented. In side-by-side comparisons conducted in Denmark, plants of the new Rose differed from plants of the cultivar Espever in the following characteristics:

1. Plants of the new Rose were not as outwardly spreading as plants of the cultivar Espever.
2. Plants of the new Rose were more freely branching and more freely flowering than plants of the cultivar Espever.
3. Flowers of plants of the new Rose had fewer petals per flower than flowers of plants of the cultivar Espever.
4. Plants of the new Rose and the cultivar Espever differed in flower coloration as plants of the cultivar Espever had lighter red-colored petals.
5. Plants of the new Rose had shorter peduncles than plants of the cultivar Espever.

BRIEF DESCRIPTION OF PHOTOGRAPHS

The accompanying colored photographs illustrate typical specimens of the vegetative growth and flowers of the new Rose plant, showing the colors as true as it is reasonably possible to obtain in colored reproductions of this type. Colors in the photographs may differ slightly from the color values cited in the detailed botanical description which more accurately describe the actual colors of the new Rose plant.

The photograph at the top of the first sheet comprises a side perspective view of typical plants of the new Rose plant grown in a container in Denmark.

The photograph at bottom of the first sheet is a side perspective view of typical plants of 'Espever' (left) and 'Evera 117' (right).

The photograph at the top of the second sheet comprises close-up views of the upper surfaces of typical flowers and leaves of the 'Espever' (left) and 'Evera 117' (right).

The photograph at the bottom of the second sheet comprises close-up views of the lower surfaces of typical flowers and leaves of the 'Espever' (left) and 'Evera 117' (right).

DETAILED BOTANICAL DESCRIPTION

The following observations and measurements describe plants grown in Denmark in 10-cm containers in a glass greenhouse and under conditions which closely approximate commercial production conditions during the summer. Plants used for the description were about 15 weeks old. In the following description, color references are made to The Royal Horticultural Society Colour Chart, 1995 Edition, except where general terms of ordinary dictionary significance are used.

Botanical classification: *Rosa hybrida* cultivar Evera 117.
Commercial classification: Potted Rose.
Parentage:
- *Female, or seed, parent.*—Unnamed proprietary seedling, not patented.
- *Male, or pollen, parent.*—Unnamed proprietary seedling, not patented.

Propagation:
- *Type.*—Terminal or stem cuttings.
- *Time to rooting.*—8 to 10 days with soil temperatures of 20° C.
- *Root description.*—Fine; freely branching.

Plant description:
- *Form.*—Upright, compact and rounded plant habit.
- *Plant height.*—About 23 cm.
- *Plant width.*—About 18 cm.
- *Growth habit.*—Moderately vigorous; suitable for 10-cm containers.
- *Stem description.*—Branching habit: About three to six lateral branches per plant. Lateral branch length: About 18 to 22 cm. Lateral branch diameter: About 4 mm. Internode length: About 1.2 to 2.5 cm. Texture: Smooth, glabrous. Color: 146B to 146C. Thorns: Length: About 3 to 5 mm. Diameter: About 3 to 5 mm. Shape: Roughly deltoid. Color: 166C.
- *Foliage description.*—Arrangement: Alternately; compound with typically three to five leaflets per leaf, generally symmetrical Leaflet length: About 2.5 to 5 cm. Leaflet width: About 1.5 to 3.6 cm. Shape: Ovate. Apex: Apiculate. Base: Obtuse. Margin: Serrulate. Venation pattern: Pinnate; reticulate. Texture, upper and lower surfaces: Smooth, glabrous; leathery. Petiole length: About 1.2 to 2 cm. Petiole diameter: About 1 mm. Color: Developing foliage, upper surface: 147A. Developing foliage, lower surface: 191A. Fully expanded foliage, upper surface: 147A. Fully expanded foliage, lower surface: 191A tinted with 187B. Venation, upper surface: 147A to 147B. Venation, lower surface: 146C. Petiole, upper and lower surfaces: 146B.

Flower description:
- *Flower type and habit.*—Large double bright red-colored flowers. Consistently symmetrical rosette flowers that are hemispherical in shape. Flowers borne singly on erect and strong peduncles; about six to eight flower buds and flowers per lateral branch. Flowers persistent.
- *Flowering season.*—Year-round under greenhouse conditions, optimal flowering from spring through autumn under garden conditions; flowering intermittent.
- *Flower diameter.*—About 5.5 to 6.5 cm.
- *Flower depth (height).*—About 1.8 cm.
- *Flower longevity on plant.*—About two weeks.
- *Fragrance.*—Slight; typical of *Rosa.*
- *Flower buds (at stage of showing color).*—Shape: Ovoid. Length: About 1.8 cm. Diameter: About 9 mm. Color: 146B.
- *Petals.*—Quantity: About 17 to 18 per flower. Length: About 0.9 to 3 cm. Width: About 0.8 to 3.6 cm. Shape: Broadly obovate. Apex: Rounded; retuse. Base: Attenuate. Margin: Entire. Texture, upper and lower surfaces: Smooth, glabrous; satiny. Color: When opening and fully opened, upper surface: 45B. When opening and fully opened, lower surface: Between 45B and 53C.
- *Sepals.*—Quantity flower: Typically five. Calyx length: About 2 to 2.2 cm. Calyx diameter: About 6 to 7 mm. Shape: Linear; falcate. Apex: Sharply pointed. Base: Truncate. Texture, upper and lower surfaces: Pubescent. Color, upper and lower surfaces: Close to 147A.
- *Peduncles.*—Strength: Strong, but flexible. Aspect: Mostly erect. Length: About 3 to 3.5 cm. Diameter: About 2 to 3 mm. Texture: Smooth, glabrous. Color: 144A.
- *Reproductive organs.*—Stamens: Quantity: About 62 per flower. Anther length: About 2 mm. Anther shape: Reniform. Anther color: 22A. Pistils: Quantity: About 32 per flower. Pistil length: About 5 to 6 mm. Stigma color: 5D. Style color: 179A to 179B.
- *Seed/fruit.*—Seed and fruit production has not been observed.

Disease/pest resistance: Plants of the new Rose have not been shown to be resistant to pathogens and pests common to Rose plants.

Temperature tolerance: Plants of the new rose have been shown to be tolerant to temperatures from 0° C. to 45° C.

It is claimed:

1. A new and distinct rose plant named 'Evera 117', as illustrated and described.

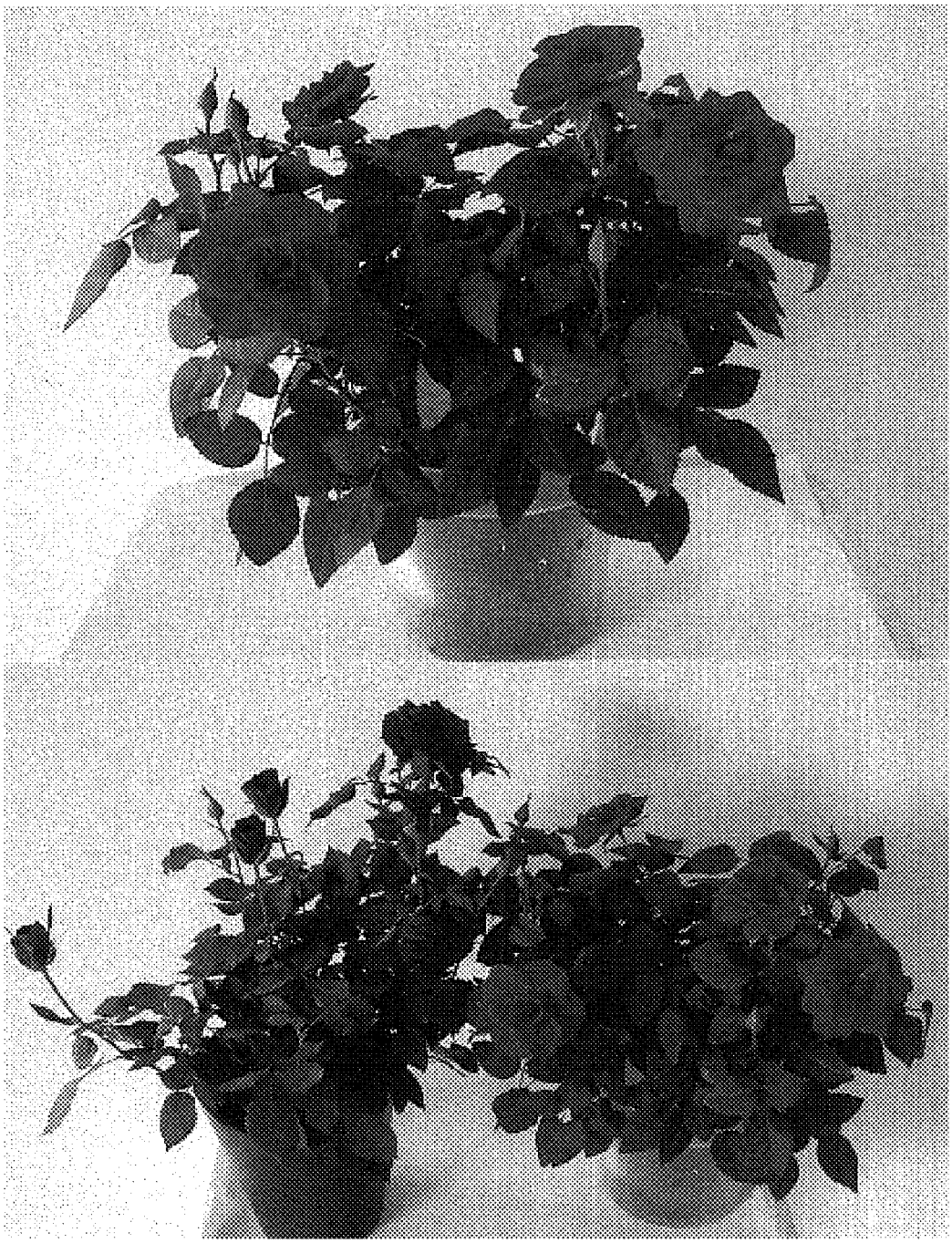

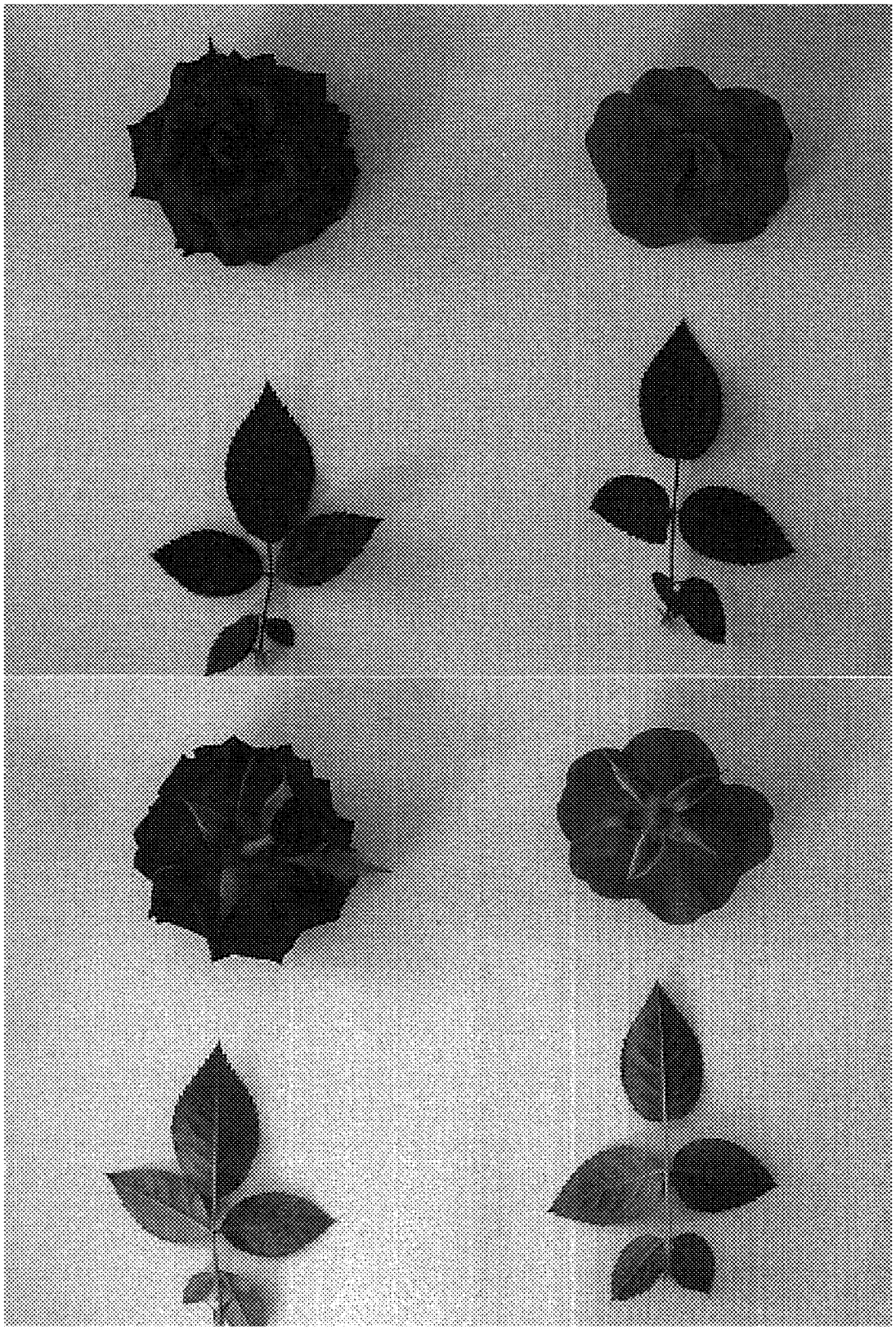

* * * * *